United States Patent [19]
Khan et al.

[11] Patent Number: 6,013,027
[45] Date of Patent: Jan. 11, 2000

[54] METHOD FOR USING A TISSUE STABILIZATION DEVICE DURING SURGERY

[75] Inventors: Jamal H. Khan, Charleston, W. Va.; Randall K. Wolf, Cincinnati, Ohio; William D. Fox, New Richmond, Ohio; Gary W. Knight, West Chester, Ohio; David L. Hamann, Cincinnati, Ohio; Craig B. Berky, Milford, Ohio

[73] Assignee: Ethicon Endo-Surgery, Inc., Cincinnati, Ohio

[21] Appl. No.: 09/115,894

[22] Filed: Jul. 15, 1998

Related U.S. Application Data

[63] Continuation-in-part of application No. 08/946,417, Oct. 7, 1997, Pat. No. 5,863,730, which is a continuation-in-part of application No. 08/946,520, Oct. 7, 1997.

[51] Int. Cl.$^7$ ...................................................... A61B 17/02
[52] U.S. Cl. ........................................... 600/201; 600/229
[58] Field of Search ..................................... 600/228, 227, 600/229, 201

[56] References Cited

U.S. PATENT DOCUMENTS

| | | |
|---|---|---|
| Re. 34,150 | 12/1992 | Santilli . |
| 2,082,782 | 6/1937 | Allen . |
| 3,626,471 | 12/1971 | Florin . |
| 4,047,532 | 9/1977 | Phillips . |
| 4,049,000 | 9/1977 | Williams . |
| 4,143,652 | 3/1979 | Meier . |
| 4,457,300 | 7/1984 | Budde . |
| 4,617,916 | 10/1986 | LeVahn . |
| 4,627,421 | 12/1986 | Symbas . |
| 4,637,377 | 1/1987 | Loop . |
| 4,726,356 | 2/1988 | Santilli . |
| 5,171,254 | 12/1992 | Sher ......................................... 606/166 |
| 5,215,526 | 6/1993 | Deniega ................................... 604/164 |
| 5,392,764 | 2/1995 | Swanson .................................... 128/3 |
| 5,545,123 | 8/1996 | Ortiz ........................................ 606/235 |
| 5,547,473 | 8/1996 | Peyman ..................................... 604/27 |
| 5,562,658 | 10/1996 | Long ......................................... 606/15 |
| 5,588,952 | 12/1996 | Dandolu ................................... 600/249 |
| 5,595,172 | 1/1997 | Reese ....................................... 128/200 |
| 5,643,217 | 7/1997 | Dobkin ..................................... 604/180 |
| 5,749,892 | 5/1998 | Vierra ....................................... 600/204 |
| 5,782,746 | 7/1998 | Wright ....................................... 600/37 |
| 5,865,730 | 2/1999 | Fox et al. ................................. 600/228 |

FOREIGN PATENT DOCUMENTS

| | | | |
|---|---|---|---|
| 0791330 | 8/1997 | European Pat. Off. ............... | 600/228 |
| WO97/10753 | 3/1997 | WIPO ............................. | A61B 17/02 |
| WO98/17182 | 4/1998 | WIPO ............................. | A61B 17/02 |

*Primary Examiner*—Paul J. Hirsch
*Attorney, Agent, or Firm*—Dean Garner

[57] ABSTRACT

A method is described for stabilizing moving tissue within the body. The method comprises creating a first opening for primary surgical access into the body, and a second opening spaced apart from the first opening in the body. An elongated stem having a proximal end and a distal end is inserted into the second opening. A foot having an upper and a lower surface is inserted into the first opening. The lower surface of the foot is engaged with the moving tissue within the body. The distal end of the stem is releaseably attached to the foot. The proximal end of the stem may be held so as to stabilize the moving tissue within the body.

18 Claims, 13 Drawing Sheets

METHOD FOR USING A TISSUE STABILIZATION DEVICE DURING SURGERY

This patent application is a continuation-in-part of U.S. Pat. application Ser. No. 08/946,417 now U.S. Pat. No. 5,863,730,(Attorney Docket No. END 489) filed on Oct. 7, 1997, which is a continuation-in-part of co-pending U.S. patent application Ser. No. 08/946,520 (Attorney Docket No. END 460) filed on Oct. 7, 1997.

FIELD OF THE INVENTION

The present invention relates to the field of surgery. More specifically, the present invention generally relates to surgical devices and methods that stabilize or temporarily immobilize moving tissue during a surgical procedure. The present invention has even further relation to such devices and methods that are used to stabilize a beating heart during cardiovascular surgery.

BACKGROUND OF THE INVENTION

There are many types of surgical procedures where the surgeon must perform various operations on moving organs or tissue within the human body. For example, there has recently been an effort to perform coronary artery bypass surgery on a beating heart, without using cardiopulmonary bypass and a heart-lung machine. During a typical coronary bypass procedure, a bypass graft is used to help reestablish coronary artery circulation when a portion of the coronary artery is stenosed. Typically the graft vessel used in bypassing the stenosed portion of the coronary artery comprises one or more segments of the patient's saphenous vein or mammary artery.

Once the graft vessel is harvested and prepared, one end is sutured to the aorta, near its base, and the other end is attached to the coronary artery, just distal to the blockage. Some surgeons choose to complete all the proximal anastomoses, to the aorta, before commencing the distal anastomoses to the coronary arteries. In contrast, others choose to complete the distal anastomoses first. Regardless of the order, when undertaking the distal anastomoses to the coronary artery, it is important that the vessel graft be held steady and adjacent the coronary artery, with a minimum of vascular trauma and a minimum of visual and surgical obstruction by instruments in the narrow operative field.

The speed of performing such anastomoses can become extremely critical as well. Often the target vessel, usually the coronary artery, is occluded during the procedure so that the anastomoses can be performed more easily. It is very important to reconnect the supply of blood to the artery as soon as possible in order to minimize or prevent damage to the patient. Blood vessels are now normally anastomosed end-to-end or end-to-side by suturing techniques.

Conventionally, to suture two vessels together, a surgeon passes the pointed tip of a curved, surgical needle, having a suture attached to the blunt end, through the graft and target vessels. Then, the surgeon grasps the tip of the needle which has been penetrated through the tissues with a needle holder and pulls the needle through the tissues, wherein the suture follows the curved path of the needle. Usually separate sutures are applied first at the heel and toe locations of the openings being joined, and then the sutures are carefully pulled in order to draw together the vessels. Each suture is securely knotted when the openings are properly abutted at the heel and toes locations. Then a series of stitches are applied, one at time, between the heel and toe stitches. The stitches are applied using care to bring the vessels together intima-to-intima without dislodging any plaque which may be on the inside of the stenosed vessel.

Needless to say, the typical manual suturing technique, described above, can become very difficult when performed on a beating heart. A hand-sutured, anastomosis procedure on a non-beating heart generally takes the skilled surgeon from ten to twenty minutes to complete. Therefore, there have been some attempts to provide a device for immobilizing the portion of the heart near the anastomosis site, so that the surgeon can more readily complete the bypass procedure. In the past the surgeon would use a pair or forceps or a metal fork-type device to push against a portion of the heart to keep it still. Obviously, this could be a tiring task for the surgical assistant to hold the forceps in place while trying to stay out of the surgeon's way during the procedure.

Another type of stabilization device is called a "vacuum based" device. Vacuum based devices have members which grab onto a portion of the heart by suction and lift it up in order to immobilize it. An example of such a device is given in PCT International Publication Number WO 97/10753, published on Mar. 27, 1997 and which is hereby incorporated herein by reference. However, this device has many disadvantages, including a low integrity vacuum seal between the device and the heart caused by any number of reasons including particulates being trapped in the vacuum tube.

SUMMARY OF THE INVENTION

In accordance with the present invention there is provided a method for stabilizing moving tissue, such as a beating heart, so as to facilitate surgical procedures on such tissue. The method comprises creating a first and a second opening into the body, wherein the first opening is the primary surgical access to the moving tissue, and the second opening is the secondary surgical access to the moving tissue. The second opening is near or adjacent the first opening and is generally much smaller than the first opening. The method further comprises inserting an elongated stem into the second opening, the stem having a distal and proximal end. The method also comprises inserting at least one foot into the first opening, and engaging the distal surface of each foot to the surface of the moving tissue within the body. The foot is attached to the distal end of the stem by a connector which may be actuated remotely on the proximal end of the stem outside the body. The proximal end of the stem is held by a mount attached to a surgical retractor or other object which is stable relative to the moving tissue within the body. The method enables the surgeon to visualize and access the moving tissue within the body through the first opening without the obstruction of the stem and mount.

BRIEF DESCRIPTION OF DRAWINGS

The foregoing and other aspects of the present invention will best be appreciated with reference to the detailed description of the invention in conjunction with the accompanying drawings, wherein.

The drawings are not necessarily to scale.

DETAILED DESCRIPTION OF THE INVENTION

In surgery on the heart or other organs of the body, the surgeon must first make an incision through several layers of tissue to achieve access to the organ, and the opening created must be held open during the duration of the surgery using an adjustable, surgical retractor. Surgical retractors are well-known in the surgical art, several examples being illustrated in U.S. Pat. Nos. 4,617,916 issued to Le Vahn et al. on Oct. 21, 1986; and 4,27,421 issued to Symbas et al on Dec. 9, 1986, both of which are hereby incorporated herein by reference. One common element of these retractors is a metal cross bar which may vary in cross-sectional dimensions, but is generally rectangular, and is about 5 mm (0.19 in.) thick by about 19 mm (0.75 in.) wide. In the case of minimally invasive, direct coronary artery bypass (MIDCAB) surgery, a mini-thoracotomy is created with an incision through the chest wall about 10 cm long running in the intercostal space between the ribs anterior to the heart. The retractor is then inserted into the narrow opening created, and the ribs and tissues are spread apart through adjustment of the retractor, thus exposing the heart.

Figure 1:
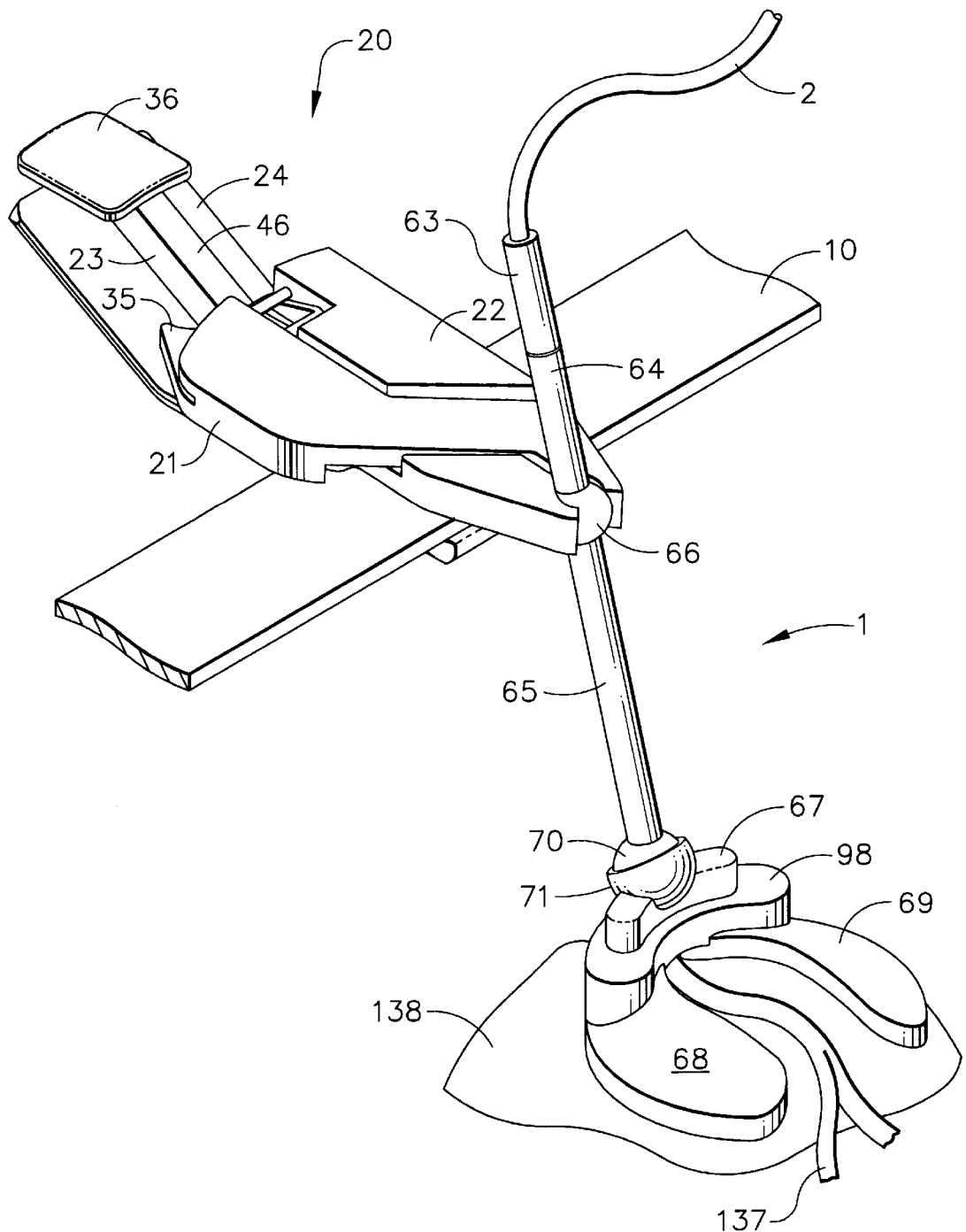
FIG. 1 is a view of the preferred embodiment of a stabilizer being used in combination with a surgical retractor (partially shown) to temporarily immobilize a local area of heart tissue in which access to the heart is achieved through a mini-thoracotomy.

FIG. 1 depicts the preferred embodiment of a stabilizer 1 and a retractor mount 20 and are shown attached to a surgical retractor cross bar 10 (partial view). The stabilizer is attached to a suction source (not shown) by a flexible hose 2. The distal portion of the stabilizer is shown in contact with the organ 138 being stabilized and consisting of a left foot 69 and a right foot 68 which in some cases may be placed to straddle a vessel 137 to be operated on. The left and right feet, 69 and 68, are somewhat like clamshells in that they are generally hollow and crescent shaped. When the organ is in complete contact with the edge along the entire perimeter of each foot, and when a suction source is communicated to each foot via air passages through the stabilizer 1, the feet, 69 and 68, maintain enhanced attachment to the organ. How much force would be required to pull the stabilizer 1 away from the organ would depend on the seal created and the negative pressure of the suction. A significant amount of stabilization of the organ would also be achieved without the suction source, however, due to how well the organ conforms to the stabilizer which is held firmly in the retractor mount 20. Again in FIG. 1, it can be seen that the stabilizer 1 is removeably attached to the retractor mount 20 which, in turn, is removably attached to the retractor cross bar 10. Also shown is distal ball 70 which allows angular and rotational movement of the distal portion of the stabilizer with respect to the lower stem 65, and a proximal ball 66 which allows rotational, angular, and longitudinal movement of the stabilizer 1 with respect to the retractor mount. As a result, it is possible to accommodate large variations in the position of the organ relative to the surgical retractor cross bar 10 location and orientation. This is important due to the wide range of surgical patient sizes, differences in anatomy, and variations in surgical technique.

Figure 2:
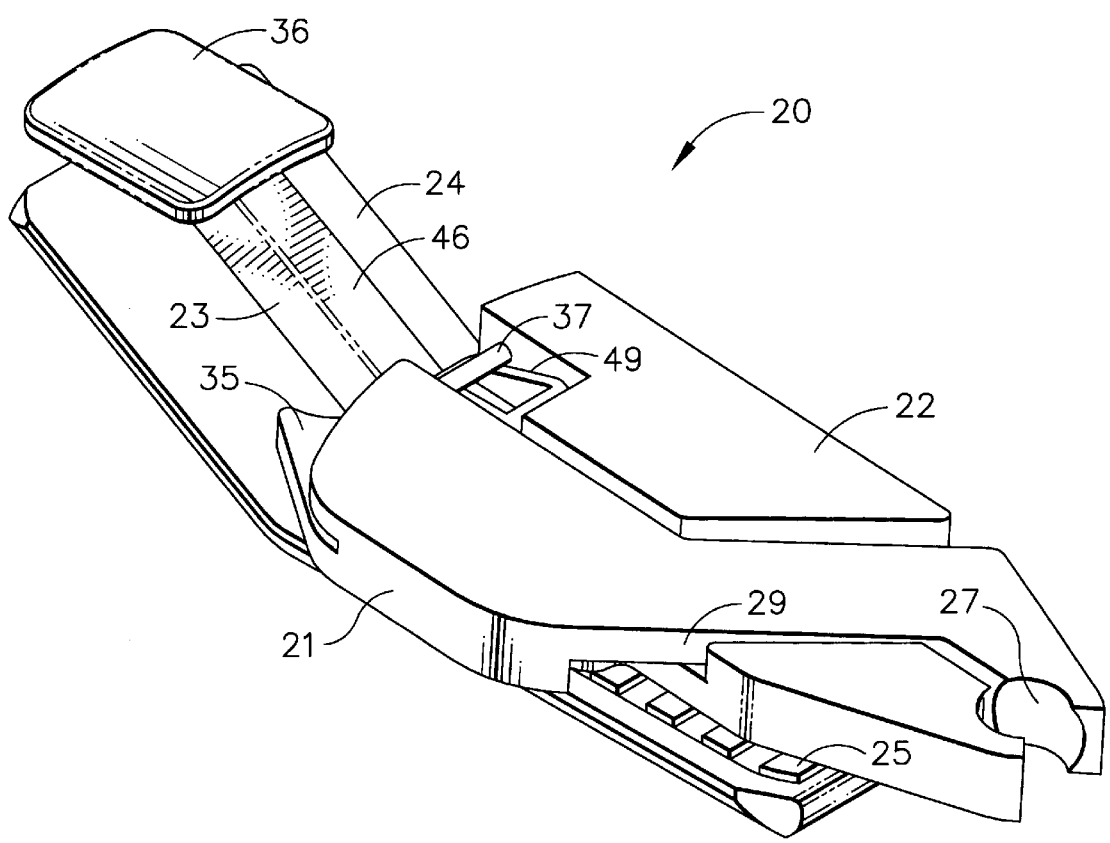
FIG. 2 is an isometric view of the stabilizer mount shown in FIG. 1.
Figure 3:
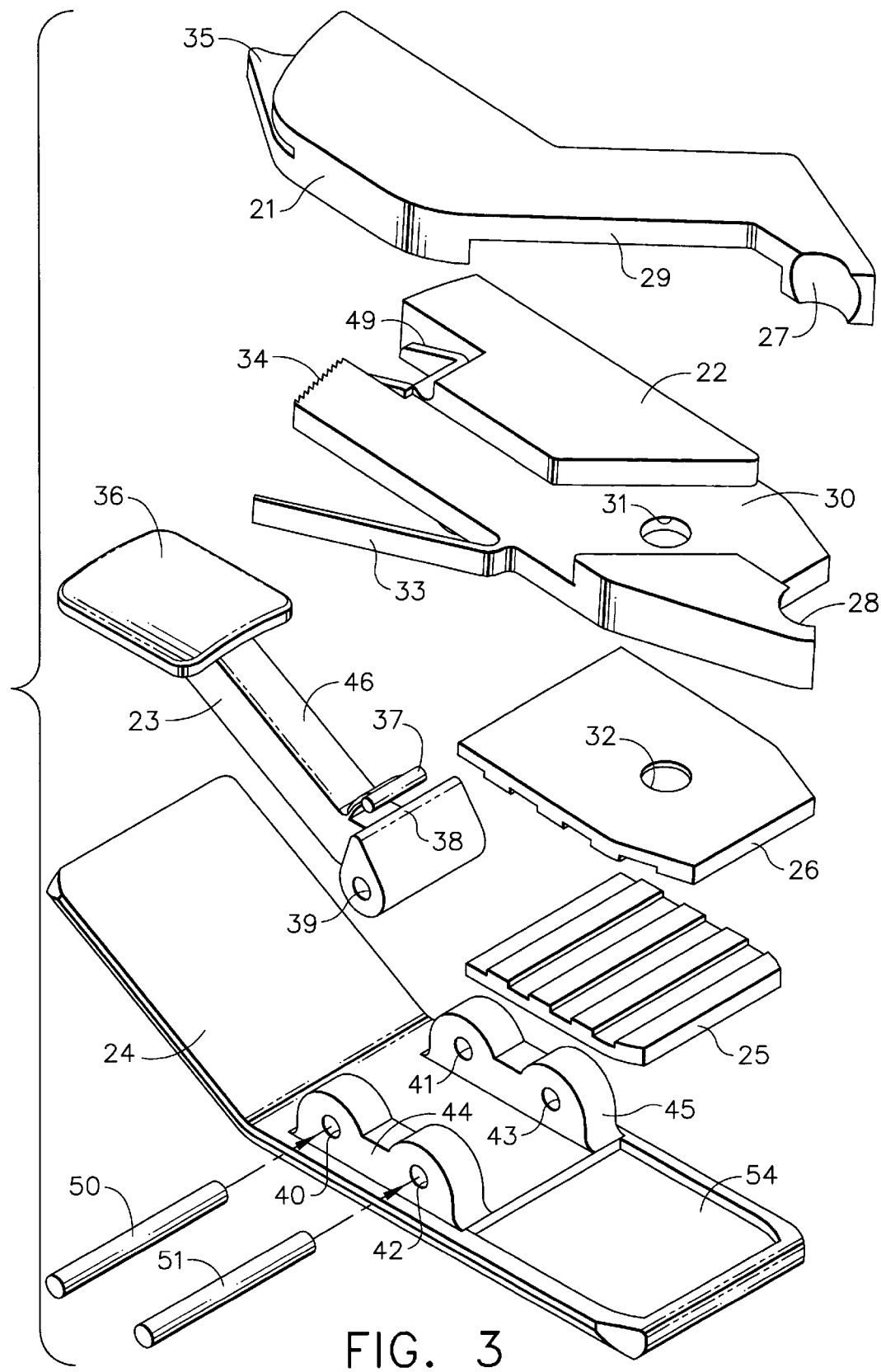
FIG. 3 is an exploded, perspective view of the components of the retractor mount depicted in FIG. 2.

Turning to FIGS. 2 and 3, the retractor mount 20 has six main components: the mount base 24, the mount top 22, the cam lever 23, the ball clamp arm 21, the upper gripping pad 26, and the lower gripping pad 25. These components may be made of metal such as a stainless steel in order to be reusable and sterilizable in a steam autoclave, but in the preferred embodiment, components 21, 22, 23, and 24 are made of a rigid, medical grade plastic. The gripping pads 25, 26 are made of a less rigid, medical grade plastic. The cam lever 23 is hinged to base 24 by first pin 50 through holes 40 and 39. Mount top 22 is hinged to the base 24 by second pin 51 through holes 42 and 52. Ball clamp arm 21 is pivotably attached to mount top 22 by an integral, spring post 53 on the mating surface of ball clamp arm 21 into hole 31 of the mount top 22. Gripping pad 25 is retained in base 24 by an undercut recess 54 in base 24. Gripping pad 26 is retained in mount top 28 by a similar means.

Figure 4:
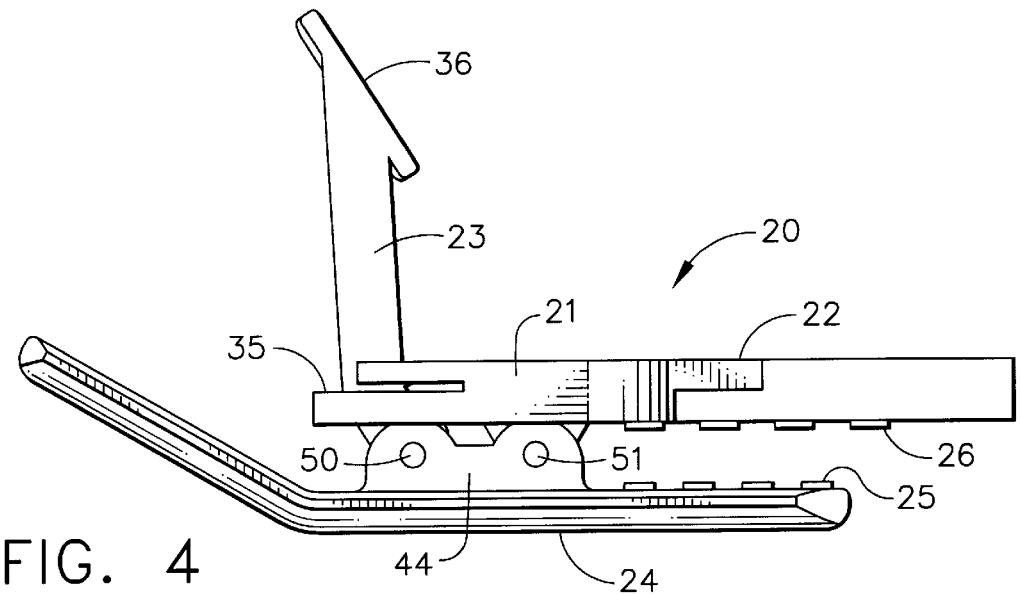
FIG. 4 is a side view of the retractor mount shown in FIG. 2.
Figure 5:
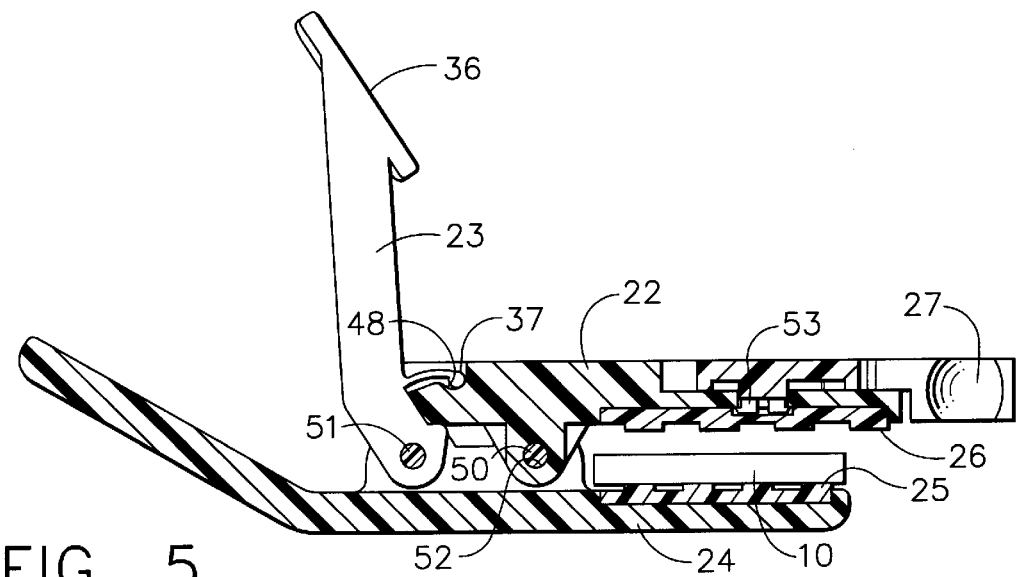
FIGS. 5 and 6 are cross-sectional views of the retractor mount depicted in FIG. 2 and show the latched and unlatched positions of the stabilizer mount as it is being attached to the retractor.
Figure 6:
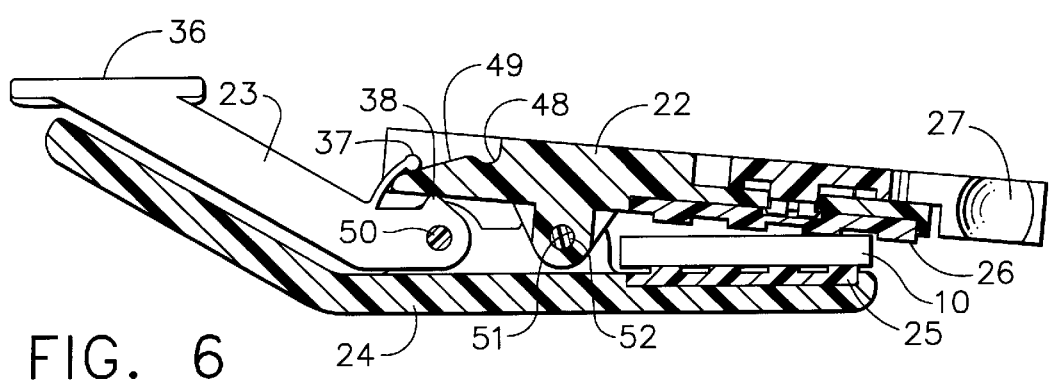

It is often necessary during the surgical procedure to reposition the stabilizer, and this may easily be accomplished in this invention by using the two adjustment features of the stabilizer mount 20. Referring now to FIGS. 4, 5, and 6, the adjustment method is described for attachment of the retractor mount 20 to the retractor cross bar 10. FIG. 4 shows the front view of the retractor mount 20 while the cam lever 23 is in the open position and before the retractor mount 20 is placed onto the cross bar 10. In FIG. 5, a longitudinal cross-section through the components except for the cam lever 23 depicts positioning of the retractor mount 20 on the cross bar 10. This view also reveals how finger 37 locates into detent recess 48 in order to hold the cam lever 23 in the open position. In this position, the mount top 22 is essentially parallel to the base 24, thus creating clearance between the gripping pads 25, 26 and the retractor cross bar 10. In FIG. 6, the cam lever 23 is shown in the closed position which is accomplished by the user squeezing lever pad 36 and base 24 together. When the cam lever beam 46 abuts base 24, cam surface 38 will have pivoted to a locking position against the underside of the mount top 22, thus causing mount top 22 to have pivoted about second pin 51 to the extent that gripping pads 25, 26 are compressed against cross bar 10. This separating force acting between the base 24 and the mount top 22 at the cross bar 10 causes the cam lever 23 to remain in the locked position so that the retractor mount cannot move about on the cross bar 10. To unlock the retractor mount 20 from the cross bar 10, an upward force may be applied by the user to the cam lever pad 36 until cam surface 38 has pivoted sufficiently to reverse the rotational moment on the cam lever 23, causing it to then pop open. During the clamping process described, the spherical clamping surface 27 of the cam lever 23 and the spherical clamping surface 28 of mount top 22 are extended beyond the edge of base 24 so that clearance is allowed for assembly of stabilizer 1 to the retractor mount 20. These spherical clamping surfaces 27, 28 are aligned in order to hold firmly onto proximal ball 66 of the stabilizer 1.

Figure 7:
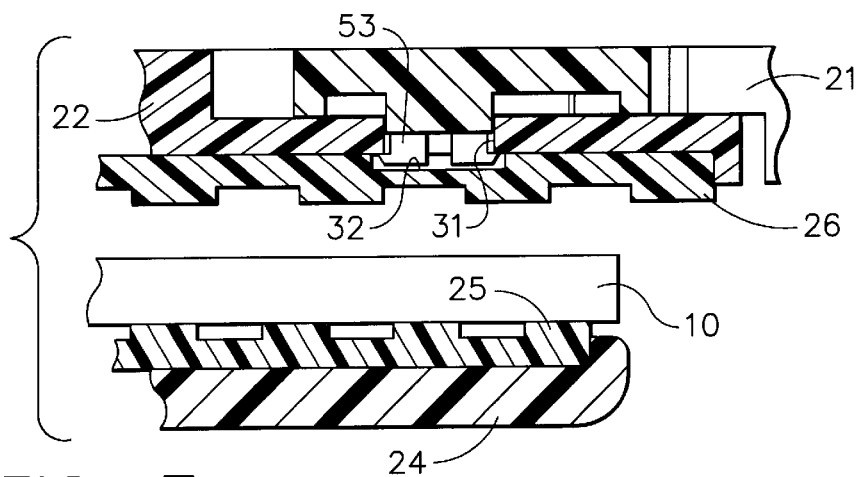
FIG. 7 is an enlarged, cross-sectional view of the retractor mount depicted in FIG. 5.

FIG. 7 shows an enlarged, cross-sectional view of the portion of the retractor mount 20 as it was depicted in FIG. 5. This view shows more clearly than in FIG. 5 the spring post 53 as it is snapped into hole 31 and partially projecting into hole 32 of gripping pad 26.

Figure 8:
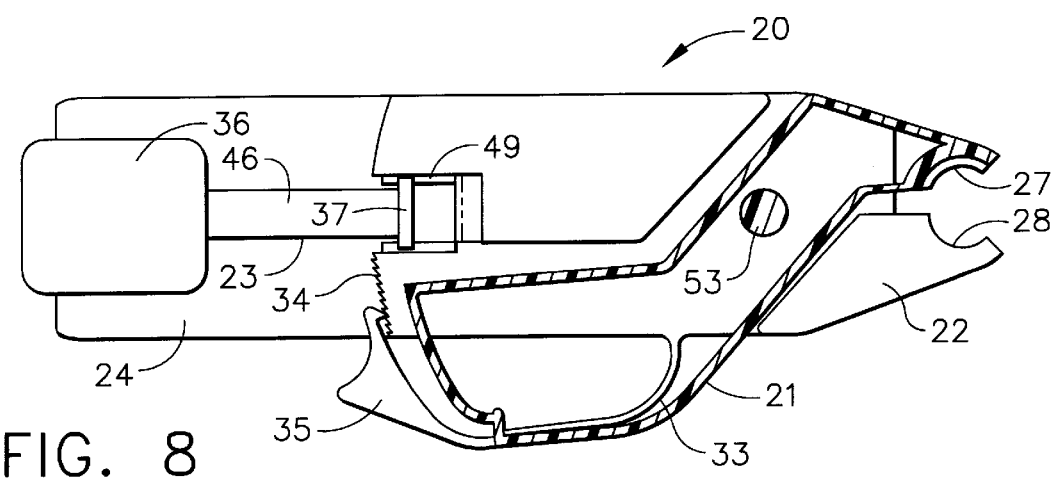
FIGS. 8 and 9 show top views of the stabilizer mount depicted in FIG. 2 and show two positions of the tightness adjustment of the retractor mount attachment to the stabilizer depicted in FIG. 1.
Figure 9:
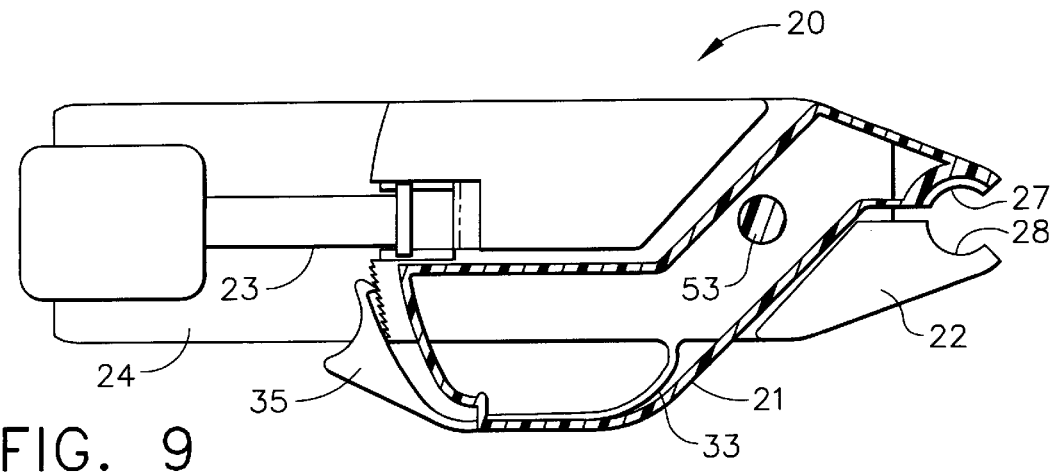

Turning now to FIGS. 8 and 9, the top view of retractor mount 20 is shown for two positions of the ball clamp arm 21, which has ratchet pawl 35 shown in engagement with ratchet teeth 34 on mount top 22. The spherical clamping surfaces 27 and 28 are seen in the open or loose position in FIG. 8 to allow movement of proximal ball 66 (FIG. 1) within. When the user squeezes ball clamp arm 21 together with mount top 22, the ball clamp arm 21 pivots about spring post 53, and the clearance between spherical surfaces 27, 28 is reduced, thus holding proximal ball 66 firmly in FIG. 9. The leaf spring 33 on the mount top 22 exerts an opening force against the ball clamp arm 21 so that when ratchet pawl 35 is pulled away from ratchet teeth 34 by the user, the ball clamp arm 21 releases the ball 66, allowing movement of the stabilizer 1 while still captured in the retractor mount 20.

Figure 10:
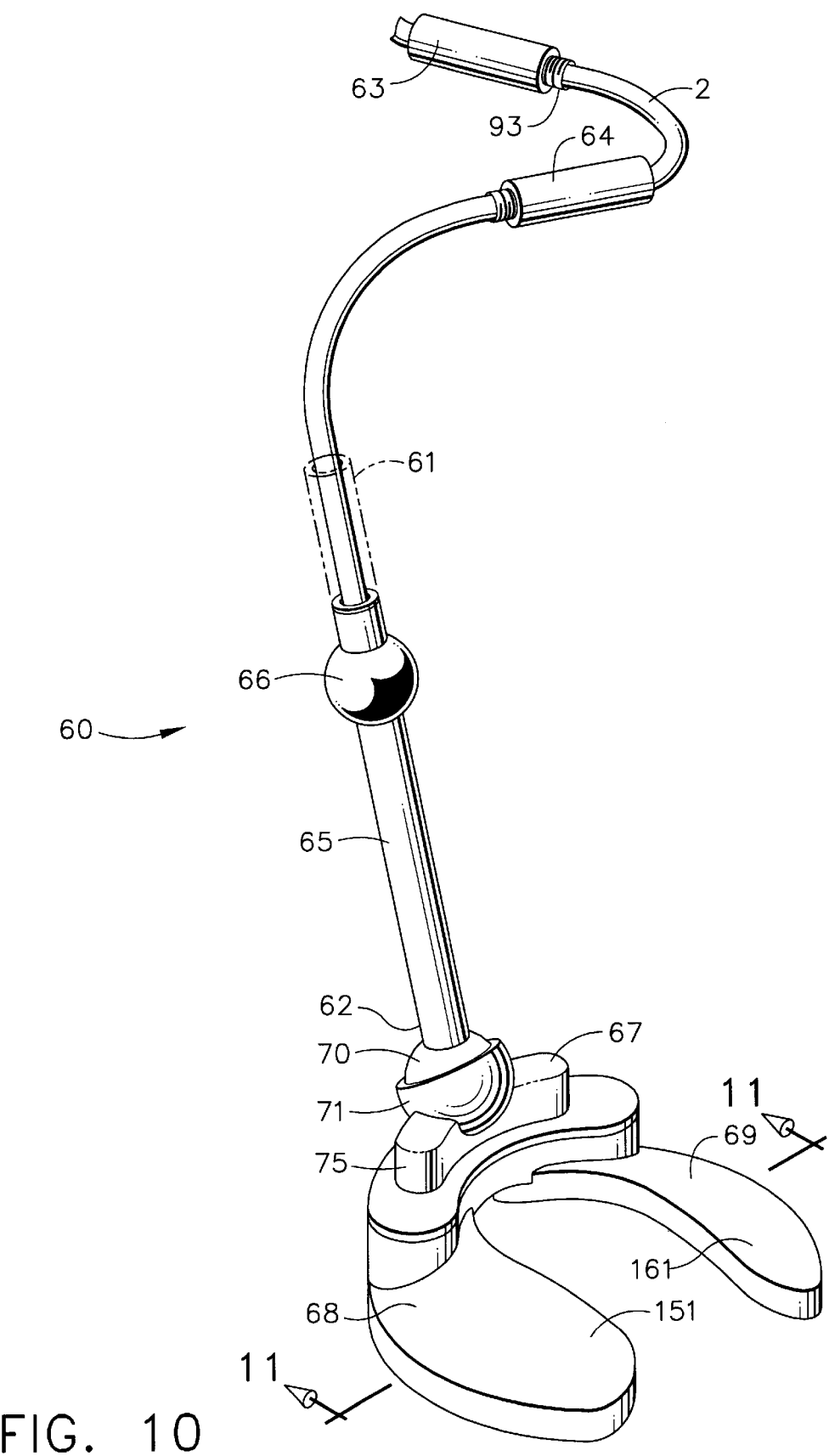
FIG. 10 is an isometric view of the stabilizer depicted in FIG. 1.

FIG. 10 shows the preferred embodiment of the stabilizer 1 which was depicted in FIG. 1. Stabilizer 1 includes a tube 60 having a proximal end 61, a distal end 62 and a lumen extending therebetween (not shown). Tube 60 is connected to a suction source by tube 2 so as to draw air from the distal end 62 to the proximal end 61. Tube 60 can include a number of stems which are detachable from each other. FIG. 10 shows tube 60 as having a first upper stem 63, a second upper stem 64 and a lower stem 65. Stem 63 has been detached from the second upper stem 64 and moved proximally on flexible hose 2. Stem 63 and 64 can be connected to each other by a threaded engagement, a frictional push fit engagement or any other means well known to those of ordinary skill in the art. FIG. 10 shows an external screw thread 93 on the distal end of the first upper stem 63 which would be attached to an internal thread on the proximal end of the second upper stem 64. The user would detach the two by rotating the first upper stem 63 while holding the second upper stem 64.

This feature allows portions of the tube 60 to be removed from the surgeons working area causing less obstruction during the procedure. The lumens through the upper stems 63, 64 are large enough to slide freely over the flexible hose 2, which is attached to the lower stem 65, and put out of the way. Second upper stem 64 can be detached from lower stem 65 in a similar manner, and moved proximally. The number of such stems may vary, depending on the desired length of the original assembly, the means of attachment to one another, and the ease of handling the individual components during a surgical procedure. Detaching these would typically be done after the adjustments on the retractor mount 20 have been made and the stabilizer feet 68, 69 are located properly on the organ. As mentioned above, this ability to detach the upper stems 63, 64 is advantageous in allowing improved access and visibility to the surgical site for the surgeon. By keeping the upper stems 63, 64 captured on the flexible hose 2, it is easy for the users (scrub nurse, etc,) to keep track of the components or to reassemble them to the stabilizer 1 during the procedure if it is determined that the overall length of the stabilizer 1 is too short.

As described earlier, the proximal ball 66 may slide freely over stems 63, 64, 65 until the ball clamp arm 21 is locked in the closed position. This is because the proximal ball 66 is made of a material, preferably plastic, which is flexible enough to be compressed onto the stems 63, 64, 65, yet the hole through it is just large enough to allow it to move freely on the stems 63, 64, 65 when not compressed. All the components of the stabilizer 1 shown in FIG. 10 may be made of metal such as stainless steel, except the flexible tube which is made of a medical grade, tubing material such as silicone or polyurethane. The preferred material for the feet 68, 69 and the bridge 75, all of which may be injected molded as one piece, is a plastic such as polycarbonate or polyethylene. This is true also for the manifold 67 and the stems 65, 64, 63. The distal end of the lower stem 65 has an integrally molded, distal ball 70 which fits tightly into a spherical cup or socket 71 feature of the manifold 67. This joint is tight enough to maintain its seal of the air passage through it and the orientation of the stabilizer 1 during the surgical procedure, yet loose enough to be adjusted easily by manipulation by the user.

Figure 11:
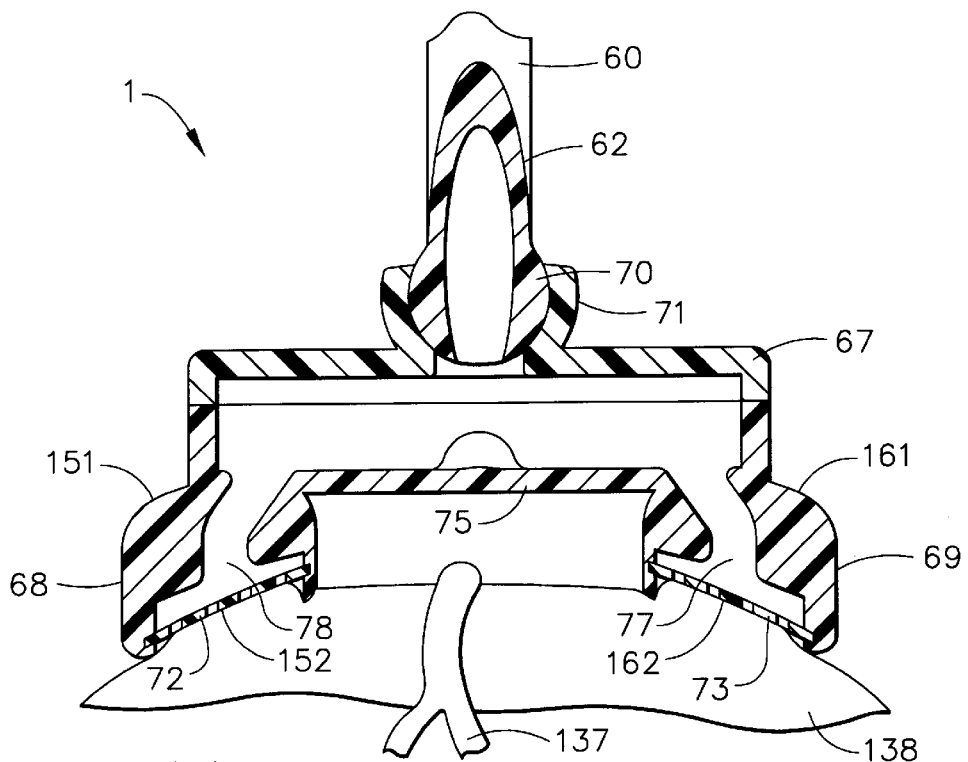
FIG. 11 shows a cross-sectional view of the distal portion of the stabilizer depicted in FIG. 10.

FIG. 11 is a cross-section of the distal portion of the stabilizer 1 shown in FIG. 10. As seen from the figure, device 1 includes at least one, and preferably a pair of feet 68 and 69, attached to the distal end 62 of tube 60. Each foot extends outwardly from tube 60. Feet 68 and 69 has a proximal surface 151 and 161, and a distal surface 152 and 162. Distal surfaces 152 and 162 make contact, direct or indirect, with the organ when in use with the vacuum. As shown in the figure surfaces 152 and 162 are in contact with an organ 138 having a vessel 137 located midway between the left and right feet 68, 69. The air passages through it can be seen as well as the left and right foot filters 73, 72 on distal surfaces 152 and 162. which are snapped into grooves in the left and right feet 69, 68 respectively. Filters 72 and 73 help prevent particulate material from entering tube 60 and causing a failure of the device.

Figure 12:
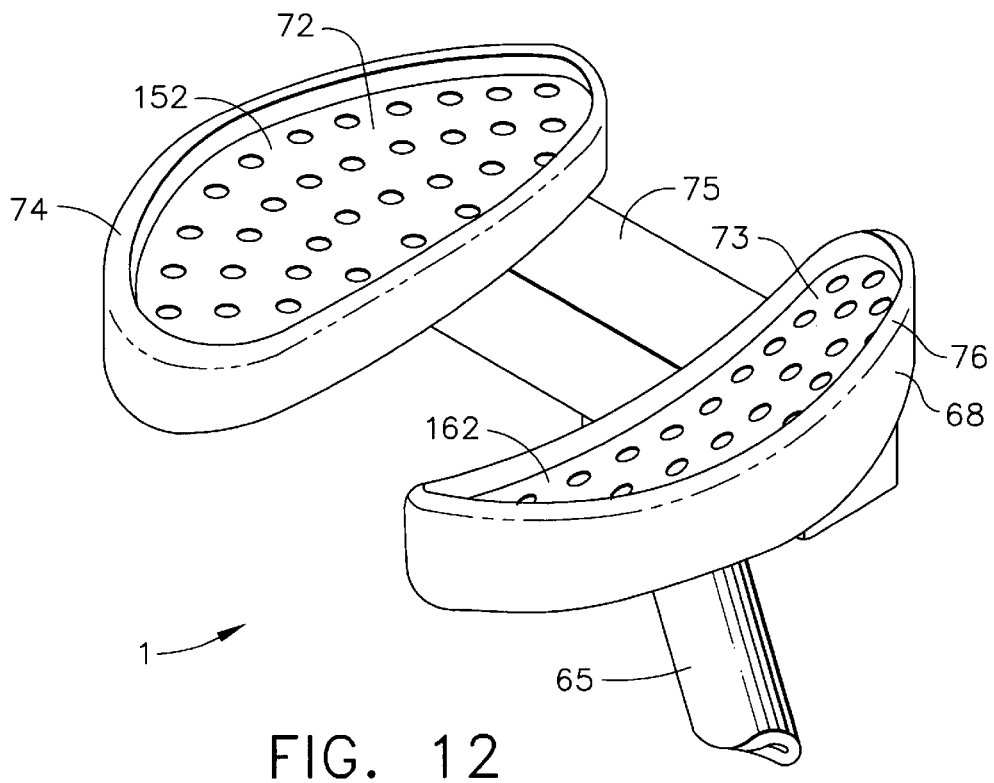
FIG. 12 is an isometric, bottom view of the distal portion of the stabilizer depicted in FIG. 1.

FIG. 12 is an isometric view of the distal portion of the stabilizer 1 of FIG. 1, giving another view of the right and left foot filters 72, 73 assembled into the feet 68, 69. The foot filters 72, 73 can be a mesh type of structure and may be a metal such as stainless steel or a plastic such as polycarbonate. They contain a plurality of holes sized largely enough and spaced in a manner to allow suction of the air from within the space between the organ surface and each screen, yet small enough to prevent tissue from blocking the suction passage through the left and right feet 68, 69.

FIGS. 11 and 12 also show how the left and right feet 69, 68 have outer perimeter edges 74, 76 which together can seal upon an essentially convex surface such as on the heart. For the enhanced attachment of the left and right feet 68, 69 to the organ surface by means of the evacuation of air and fluids from within, it is preferred that the feet perimeter edges 74, 76 remain in contact with the organ as it moves or is being manipulated. The embodiment shown in FIGS. 11, 12 has the feet perimeter edges 74, 76 defining a partial, spherical surface, that is they have a spherical profile, which has a radius of about the size of an orange, but this concavity may also vary in its depth and configuration. Another advantage of this embodiment is that the surface of the tissue in the span between the left and right feet 68, 69 is tensioned slightly, thus further stabilizing the vessel 137 or other tissue of interest to the surgeon.

Figure 16:
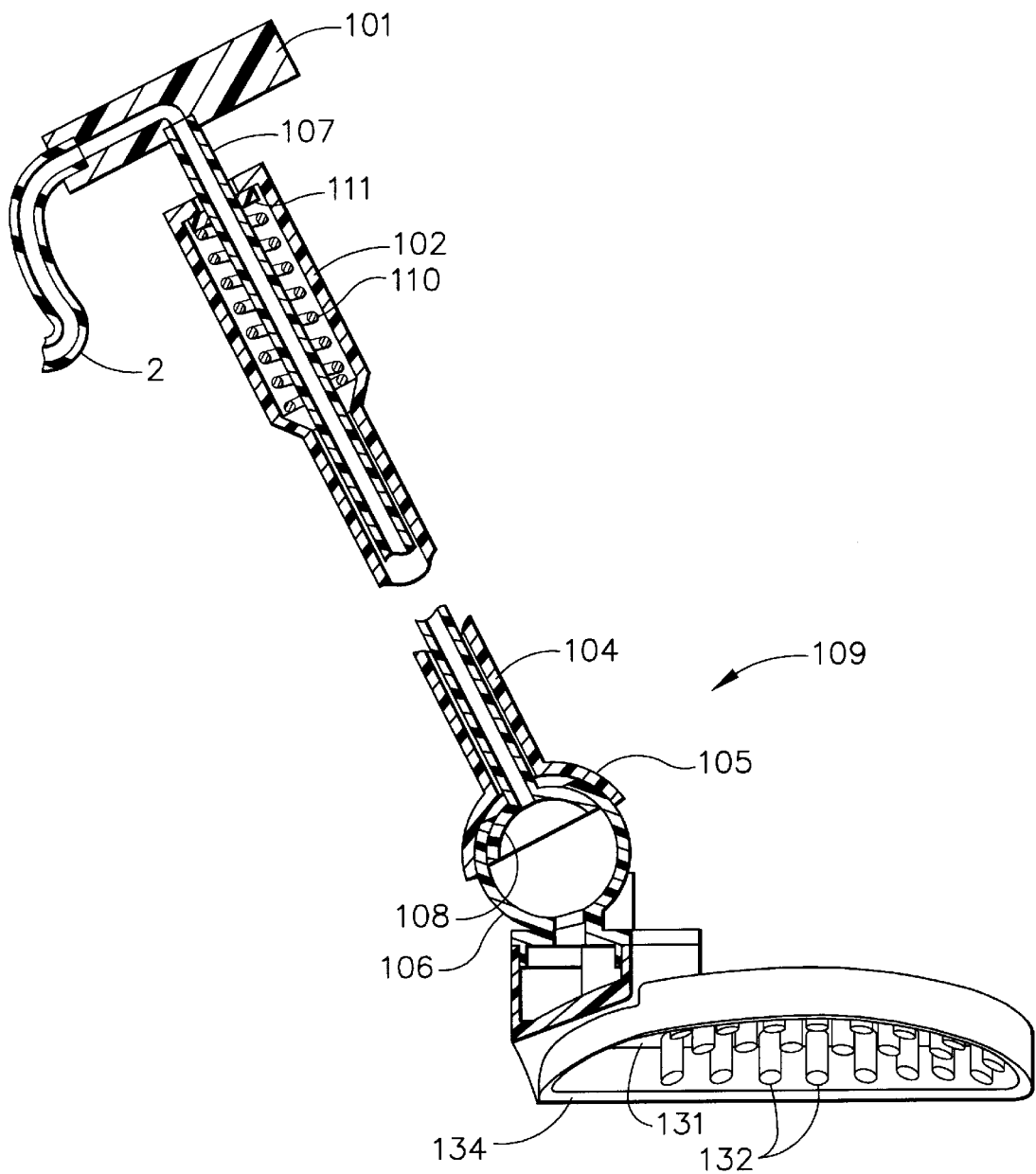
FIG. 16 is a cross-sectional view of the third embodiment of the stabilizer shown in FIG. 15.

Skipping briefly to FIG. 16, there is a third embodiment of the distal portion of the present invention. Separate components for holding tissue away from the suction orifices 133, 134 have been eliminated by the addition of a plurality of pegs extending outwardly from the proximal surface of the feet 130 and 131. The pegs 132 are preferably cylindrical and parallel to one another as shown in this embodiment, but may vary in size, spacing, and orientation. The tips extend to a length slightly proximal to the imaginary, concave surface described and provide atraumatic contact with the organ as it is pulled into the feet 130, 131 by the suction force. The surface of the organ 138 may tent into the interstitial spaces between the projections 132, thus adding the benefit of increased resistance to sliding of the stabilizer feet 130, 131 in the side-to-side directions. The projections 132 are spaced sufficiently distant from perimeter edges 74, 76 to allow the organ surface to seal properly against the left and right feet 69, 68. In addition, the pegs create a tortuous path for any particulates and therefore also act as a filter.

Figure 13:
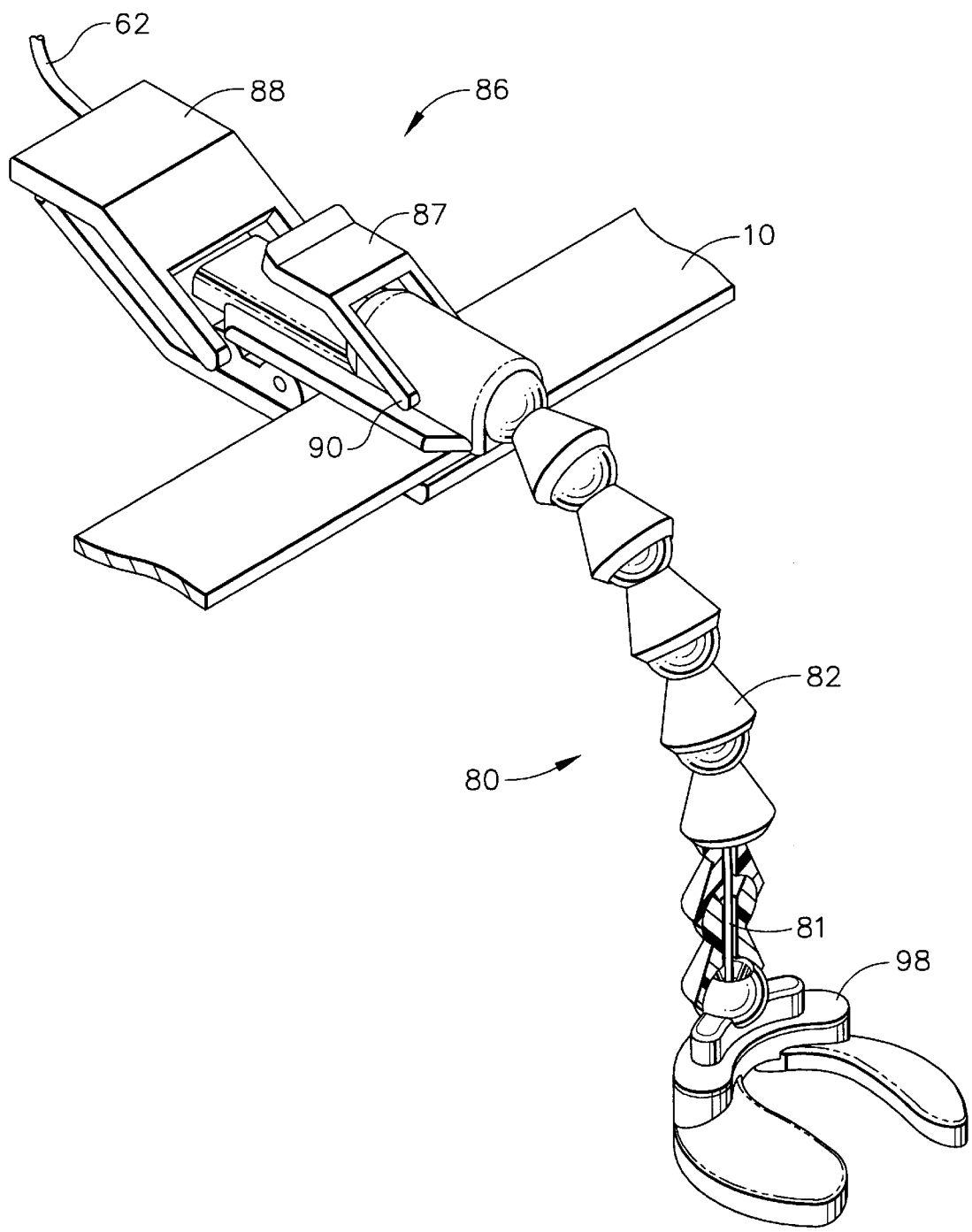
FIG. 13 shows a second embodiment of the stabilizer while it is attached to a retractor (partial view), showing a gooseneck style stabilizer connected to a draw latch stabilizer mount.
Figure 14:
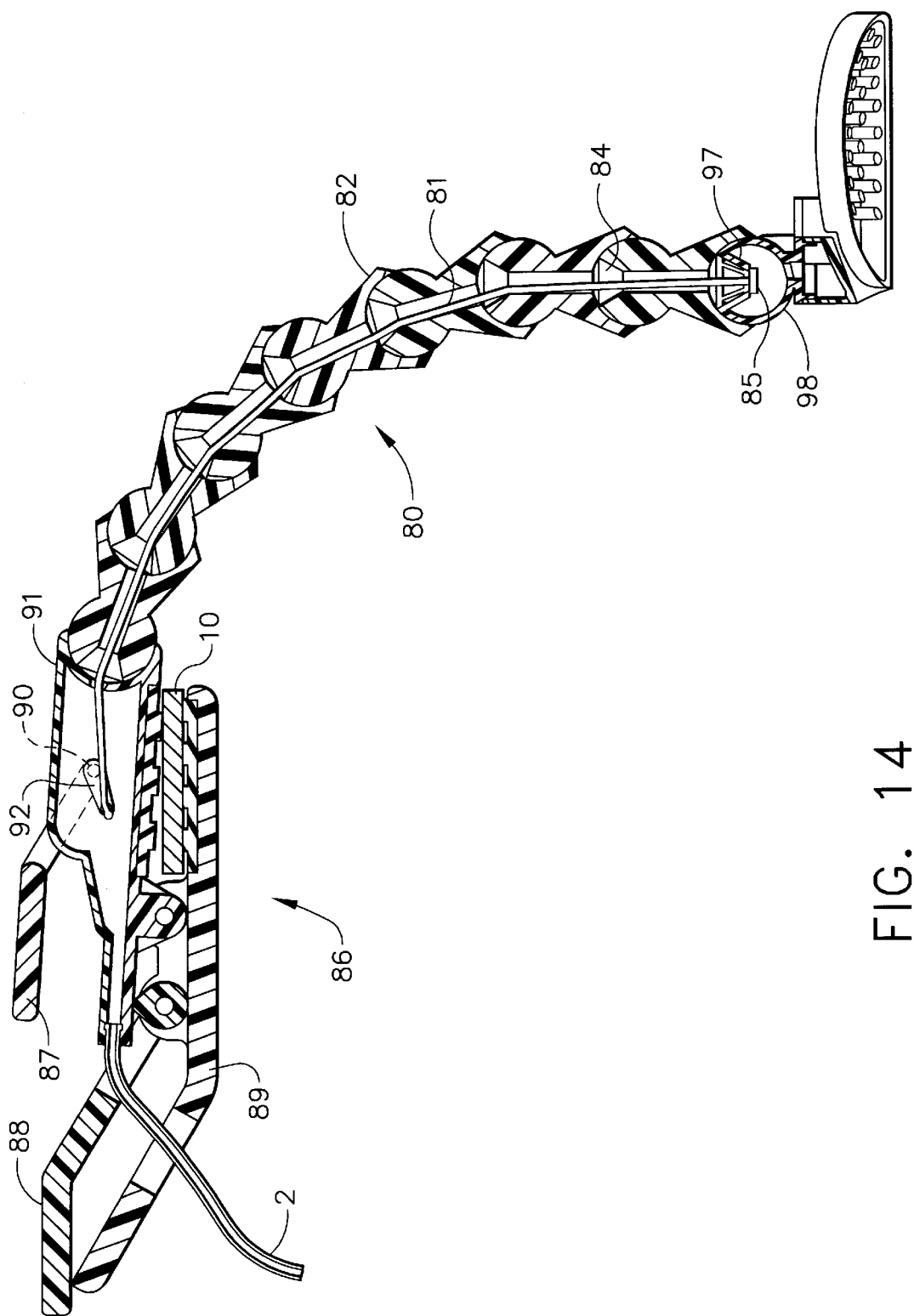
FIG. 14 shows a cross-sectional view of the second embodiment of the stabilizer depicted in FIG. 13.

Now going back to FIG. 13, there is an isometric view of a second embodiment of the present invention. The primary difference of the second embodiment from the preferred embodiment shown in FIG. 1 is the increased, positional flexibility, due to gooseneck 80 consisting of a plurality of ball/socket elements 82. A retractor mount 86 clamps onto the retractor crossbar 10 as before using cam lever 88, but the mount differs in that it has a draw latch 87 for tensioning/releasing cable 81 for locking/unlocking the hold for the orientation of the gooseneck 80. FIG. 14 further depicts this embodiment, showing the air passages within and the interactions of the components as the retractor mount is clamped onto crossbar 10 and the gooseneck 80 is locked into orientation. The distal end of cable 85 is terminated with swaged fitting 85 which abuts against an internal retention feature 97 of the manifold 98. Tension in cable 81 is created when draw latch 87 is squeezed against base 89, pivoting about draw latch pivot 90, causing draw latch hook 92 to swing over center of pivot 90. Reversal of this process releases the tension and allows the surgeon to reposition the gooseneck 80. In this embodiment, flexible hose 2 is attached to mount top 91. The number and size of ball/socket elements may vary and may be made of metal or plastic.

Figure 15:
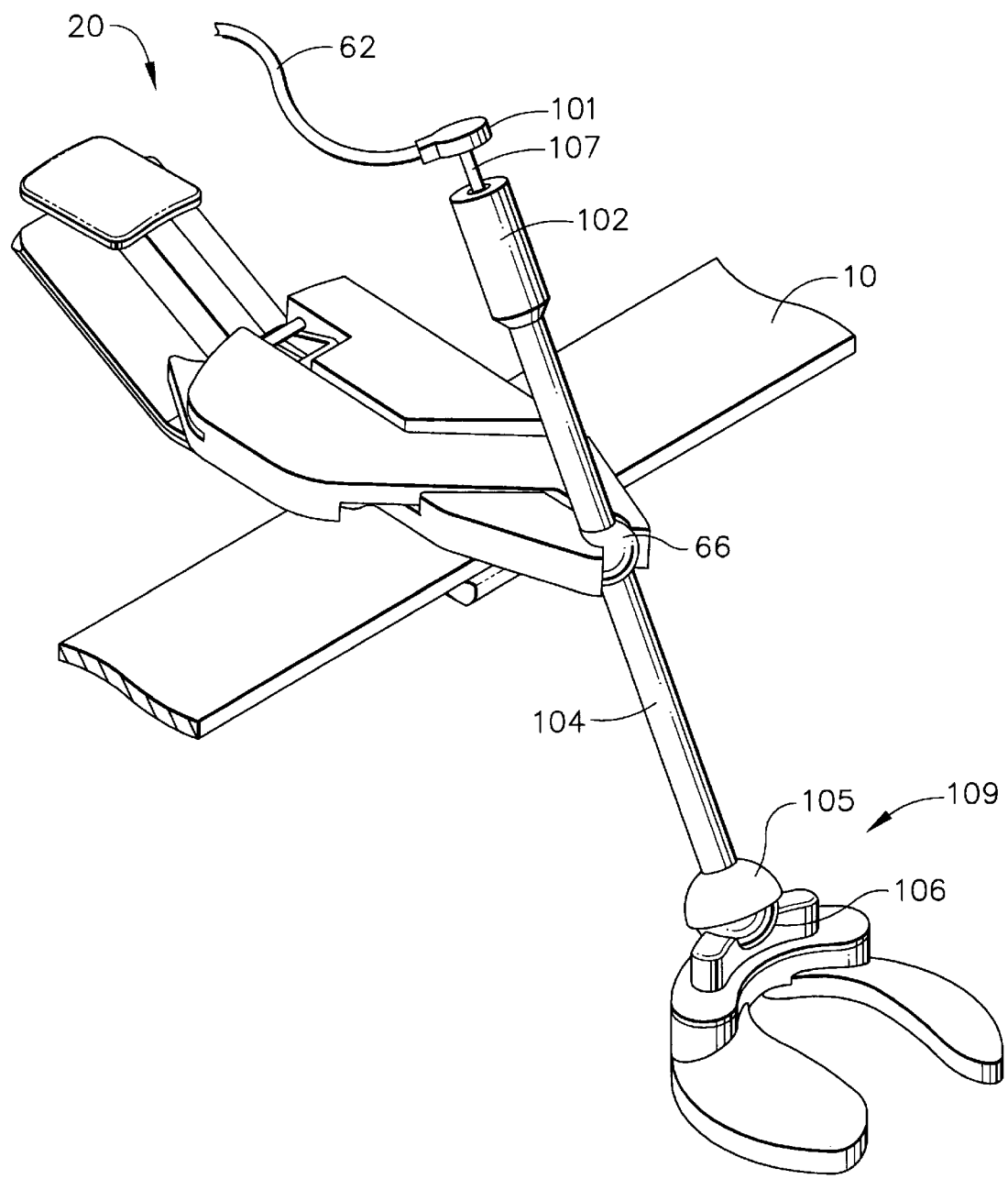
FIG. 15 shows an isometric view of a third embodiment of the stabilizer.

Referring to FIG. 15, the third embodiment referred to earlier in FIG. 16 is shown in isometric view. A remote actuator 101 has been provided for locking the ball joint 109 on the distal end of the shaft 104. The surgeon can release the tightness of the ball joint 109 by squeezing together remote actuator 101 and shaft proximal end 102. Upon release, the ball joint 109 is tight again and the stabilizer maintains its orientation. Referring again to FIG. 16, there is shown a cross-sectional view of the embodiment depicted in FIG. 15, also showing the air passage through it. The locking force is provided by coil spring 110 pushing on shaft flange 79. The stabilizer orientation is maintained by the frictional forces between components 105, 106, and 108 which are the shaft cup, manifold cup, and bell flange 108 on the distal end of shaft 107. A proximal ball 66 slides and rotates freely on shaft 104 in a similar manner as described in the preferred embodiment in FIG. 1. The retractor mount used for this embodiment would be the same as the one described in the preferred embodiment of FIG. 1. Flexible hose 2 attaches to remote actuator 101. Providing an actuator for ball and socket joint 109, which is remote, or proximal to the joint 109 is advantageous for the surgeon. The surgeons hands do not need to be placed close to organ being operated on, which could risk accidental contact and would obstruct the view.

Figure 17:
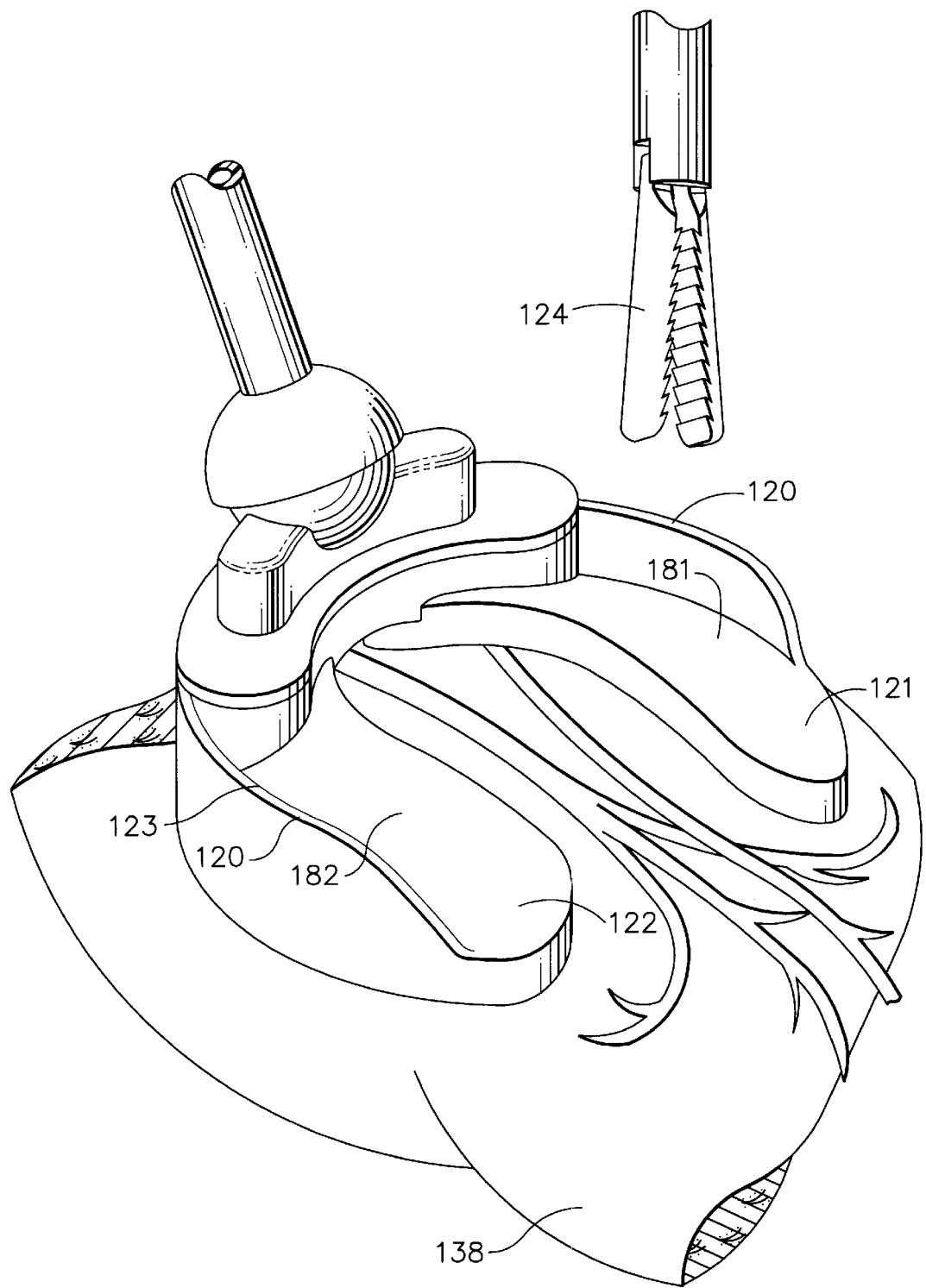
FIG. 17 shows a fourth embodiment of the distal portion of the stabilizer depicted in FIG. 2 as it is used in combination with a second, surgical, grasping device in surgery.

FIG. 17 is an isometric view of the distal portion of a fourth embodiment of a stabilizer, being used in combination with a second, surgical grasping instrument 124 for heart stabilization. In this embodiment, left and right flanges 123 and 120 have been added to the left and right feet 121, 122. Flanges 123 and 120 extend from proximal to the proximal surface 181 and 182 of the feet. The flanges provide a means of repositioning the distal portion of the stabilizer on the heart. Using the grasping instrument 124 allows the surgeon enhanced access and visibility to the surgical site, and aids in the precise positioning of the stabilizer feet. This is especially advantageous when operating through a narrow incision in the chest wall such as a mini-thoracotomy.

To further assist in the stabilization of the heart or other organ, other access retractors may also be used in conjunction with the present invention, such as spoon shaped probes to move other tissue from the surgical site.

Figure 18:
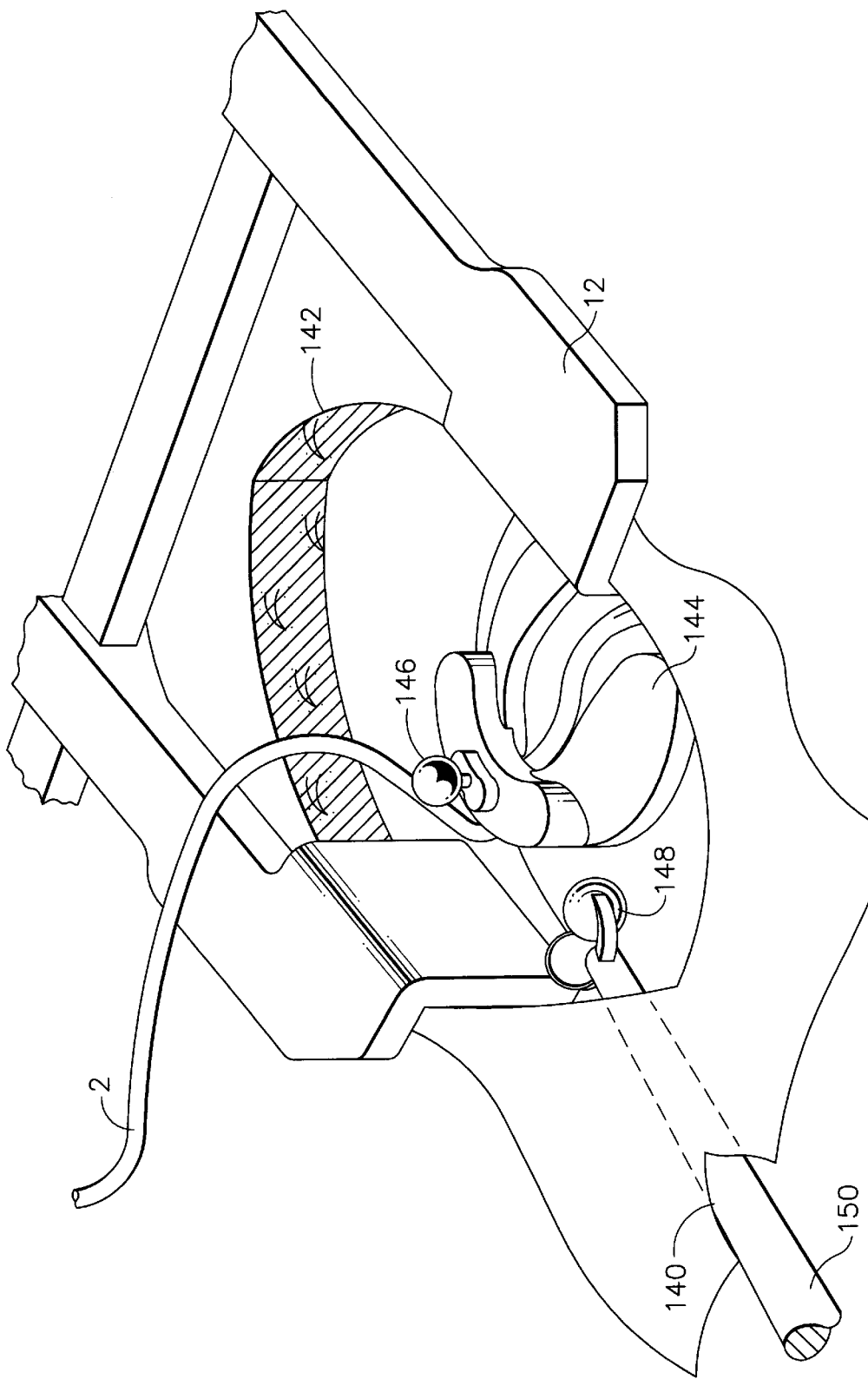
FIG. 18 is an isometric view of a fifth embodiment of the distal portion of the stabilizer, showing the stem of the stabilizer being introduced into the body through a separate, secondary opening near a primary opening into the body, and the stabilizer feet engaging the moving heart within the body, but the feet not yet attached to the distal end of the stem.

A fifth embodiment of the stabilizer is depicted in FIG. 18. In this embodiment, the stem assembly 150 (also referred to simply as a stem) is detachable from the stabilizer foot assembly 144 so that the stem assembly may be introduced into the body and to the wound site through a separate, smaller incision 140 (also referred to as a second opening) adjacent to the main incision 142 (also referred to as a first opening). Once inserted, the stem assembly 150 is attached to stabilizer foot assembly 144 by means of a pair of cup-shaped graspers 148 clamping onto ball joint 146 or by various other means which allow angular variation of the stem assembly 150 with respect to the stabilizer foot assembly 144. The graspers 148 and the ball joint 146 are also referred to as a connector. The graspers 148 may be remotely actuated to open or close by a mechanism on the proximal portion of the stem assembly by various means also, such as is commonly used for endoscopic graspers and needle holders. It can be seen in FIG. 18 that the stabilizing foot assembly 144 is optionally attached directly to a flexible, suction hose to enhance the attachment of the foot assembly 144 to the organ. The stem assembly 150 may be hand held by the surgeon's assistant in order to stabilize the organ during the surgical procedure. It may also be held by a supporting mount or structure attached to the side of the surgical table, such mounts being well-known in the surgical art. It may also be used in combination with a trocar cannula with or without screwthreads to attach to the body wall, or with other kinds of trocars well known in the art. U.S. Pat. No. 5,215,526 issued to Deniega, et al, on Jun. 1, 1993, describes a trocar which may be used in this surgical method and is incorporated herein. The advantage of using a trocar cannula to receive the stabilizing stem is that it provides an access port to the inside of the body while protecting the tissue from trauma associated with manipulating the stem through the port.

The proximal portion of stem assembly 150 may also be removably attached to the retractor 12 or other relatively stationary structures by means of various fixation devices which could easily be devised by those skilled in the art. The principal advantage of the fifth embodiment shown in FIG. 18 is that the access to and visibility of the surgical site on the stabilized organ is improved because of the absence of the stem assembly 150 in the primary incision (or first opening) 142.

The smaller incision 140 may be made by a scalpel or a trocar. Then the stem may be inserted. A novel variation of the present invention is to eliminate the step for creating the second incision 140 before insertion of the stem 150 by using a stem having a sharpened distal end. The stem could then be used to pierce through the tissue wall near the primary incision, care being taken to insure that the underlying organs are protected from the sharp tip of the stem as it enters the body cavity. This is easily accomplished since the larger primary incision has already been made, and the surgeon can reach inside to feel the piercing stem protruding through the tissue wall and controllably guide its entry into the body cavity. Then the distal end of the stem could be attached to the foot by a specially adapted coupling. For example, the distal end of the stem may have a threaded portion immediately proximal to a tapered point. This threaded portion could then be screwed into a threaded hole on the specially adapted coupling on the foot.

A further variation of the present invention is the incorporation of more than one stem for stabilizing the foot in order to increase the stability achievable for the particularly organ to which the device is applied. The combined use of multiple stems provides a sort of truss work to increase the rigidity of the stabilizing system. Each stem would be placed through the body wall percutaneously and at spaced apart locations near the primary incision, and then the distal ends of the stems could be releaseably attached to the foot. Obviously, the increase in the number of stems attached must be matched by an increase in the number of attachment points on the foot. This can be accomplished by having multiple ball joint connections on the upper surface of the foot, as may be easily incorporated into the design shown in FIG. 17 by those skilled in the art. Or it may be accomplished by having a plurality of threaded holes in the foot coupling which has been specially adapted to receive stems having threaded and sharpened ends as previously described.

As disclosed, the present invention relates to a method and apparatus for stabilizing tissue. In the preferred embodiment, the invention is used to stabilize the heart tissue for a coronary artery bypass graft procedure using a surgical retractor, without the need for a cardiopulmonary bypass. The present invention and its alternate embodiments can be used for other surgical procedures, however, such as on organs such as stomach, lungs, etc. The stabilization device and its alternate embodiments, and the method of using them, have been described in detail, but it should be understood that variations and modifications can be incorporated within the scope of the following claims. These modifications may include substituting elements or components which have the same function to achieve the same result for those described herein.

What is claimed is:

1. A method for stabilizing moving tissue within the body, said method comprising:
   a) creating a primary opening in the body for surgical access to the moving tissue within the body;
   b) creating a secondary opening in the body which is smaller than said primary opening, said secondary opening spaced apart from said first opening, for access to the moving tissue within the body;
   c) inserting an elongated stem, having a proximal end and a distal end, into said secondary opening;
   d) inserting through said primary opening a foot having an upper surface and a lower surface; and
   e) engaging the surface of the moving tissue within the body with said lower surface of said foot, releaseably attaching said foot to said distal end of said stem.

2. The method of claim 1 wherein said primary opening created is larger than said secondary opening.

3. The method of claim 1 further including the step of operating said stem so that said foot presses against the surface of the moving tissue to better stabilize the tissue.

4. The method of claim 1 wherein said stem has a lumen extending therethrough which communicates with said bottom surface of said foot, said method further including the step of connecting said stem to a vacuum source.

5. The method of claim 1 further including the step of attaching said proximal end of said stem to a holding means.

6. The method of claim 1 further including the step of inserting a trocar cannula into said secondary opening, wherein said trocar cannula is for receiving said stem.

7. The method of claim 1 wherein said step of creating said first incision comprises performing a thoracotomy.

8. The method of claim 1 further including the step of creating more than one secondary opening and inserting additional stems therethrough, and attaching distal ends of said additional stems to said foot.

9. A method for stabilizing a beating heart so as to perform a surgical procedure thereon, said method comprising:
   a) performing a thoracotomy on the body, thereby creating surgical access to the beating heart within the body;
   b) creating a secondary opening in the body which is smaller than said first opening, said secondary opening spaced apart from said first opening, said second opening also giving access to the beating heart;
   c) inserting a distal end of an elongated stem into and through said secondary opening;
   d) inserting through said primary opening a housing, said housing comprising a pair of spaced apart feet having upper surfaces and lower surfaces;
   e) engaging the surface of the beating heart with said lower surfaces of said feet such that an artery of the heart is placed between said feet; and
   f) releaseably attaching said housing to said distal end of said stem.

10. The method of claim 9 further including the step of operating said stem so that said foot presses against the surface of the moving tissue to better stabilize the tissue.

11. The method of claim 9 wherein said stem has a lumen extending therethrough which communicates with said bottom surface of each said foot, said method further including the step of connecting said stem to a vacuum source.

12. The method of claim 9 further including the step of attaching said proximal end of said stem to a surgical retractor.

13. The method of claim 9 further including the step of inserting a trocar cannula into said secondary opening, wherein said trocar cannula is for receiving said stem.

14. The method of claim 9 wherein said step of creating said first incision comprises performing a thoracotomy.

15. A method for stabilizing moving tissue within the body, said method comprising:
   a) creating a primary opening in the body for surgical access to the moving tissue within the body;

b) creating a secondary opening in the body which is smaller than said first opening, said secondary opening spaced apart from said first opening, for access to the moving tissue within the body;

c) inserting an elongated stem, having a proximal end and a distal end, into said secondary opening;

d) inserting through said primary opening a foot having an upper surface and a lower surface;

e) engaging the surface of the moving tissue within the body with said lower surface of said foot;

f) attaching said foot to said distal end of said stem; and g) attaching said stem to a surgical retractor.

16. The method of claim 15 wherein said stem has a lumen which communicates with said bottom surface of said foot, said method further including the step of connecting said stem to a vacuum source.

17. The method of claim 15 further including the step of attaching said proximal end of said stem to a holding means.

18. The method of claim 15 wherein said distal end of said stem has a grasper which grasps onto a ball joint of said foot, said step of attaching said foot to said distal end of said stem including closing said grasper onto said ball joint of said foot.

* * * * *